United States Patent [19]

Pieniak et al.

[11] Patent Number: 4,573,991

[45] Date of Patent: Mar. 4, 1986

[54] GATHERABLE LAMINATED STRUCTURE INCLUDING AN APERTURED ELASTIC MEMBER

[75] Inventors: Heinz A. Pieniak, North Brunswick, N.J.; Virginia R. Mesek, Oak Forest, Ill.

[73] Assignee: Personal Products Company, Milltown, N.J.

[21] Appl. No.: 633,568

[22] Filed: Jul. 23, 1984

Related U.S. Application Data

[63] Continuation of Ser. No. 386,451, Jun. 8, 1982, abandoned, which is a continuation-in-part of Ser. No. 210,507, Nov. 26, 1980, abandoned, which is a continuation-in-part of Ser. No. 134,369, Mar. 27, 1980, abandoned, which is a continuation-in-part of Ser. No. 60,704, Jul. 27, 1979, abandoned.

[51] Int. Cl.⁴ .............................................. A61F 13/16
[52] U.S. Cl. .............................. 604/385 A; 604/366
[58] Field of Search ................... 604/385 A, 370, 366

[56] References Cited

U.S. PATENT DOCUMENTS

| | | | |
|---|---|---|---|
| 2,748,772 | 6/1956 | Titone et al. | 604/396 |
| 3,237,625 | 3/1966 | Johnson | 604/396 |
| 3,639,917 | 2/1972 | Althouse | 2/270 |
| 3,732,576 | 5/1973 | Gauther | 2/221 |
| 3,860,003 | 1/1975 | Buell | 604/385 |
| 3,965,943 | 6/1976 | Goff, Jr. et al. | 2/237 |
| 4,050,462 | 9/1977 | Woon et al. | 604/396 |
| 4,062,995 | 12/1977 | Korpman | 428/134 |

Primary Examiner—C. Fred Rosenbaum
Assistant Examiner—Sherri E. Vinyard
Attorney, Agent, or Firm—Martha A. Michaels

[57] ABSTRACT

A laminated structure adapted to be gathered for improved fit about a portion of the human body, said laminated structure comprising an elastic member disposed between first and second substrates of flexible gatherable material, said elastic member including a plurality of interconnected elastic elements defining apertures therebetween, and the first and second substrates of said laminated structure being secured together through at least some of said apertures.

7 Claims, 14 Drawing Figures

GATHERABLE LAMINATED STRUCTURE INCLUDING AN APERTURED ELASTIC MEMBER

This application is a continuation of application Ser. No. 386,451, filed June 8, 1982, now abandoned which is a continuation-in-part application of co-pending application Ser. No. 210,507, filed Nov. 26, 1980, now abandoned which is a continuation-in-part application of co-pending application Ser. No. 134,369, filed Mar. 27, 1980, now abandoned which is a continuation-in-part application of co-pending application Ser. No. 60,704, filed July. 27, 1979 now abandoned.

BACKGROUND OF THE INVENTION

Recent years have seen an increased demand for inexpensive apparel and the development of new and inexpensive components of construction and methods of construction of articles of apparel. In certain instances, there is a demand for apparel that is very inexpensive, and indeed disposable. New elastomeric materials and methods of incorporating them into portions of a garment have been developed to meet the desire to fit these types of garments to a human form. For example, U.S. Pat. No. 3,639,917 discloses the use of a strip of a *heat recoverable* elastomeric material to gather the cuff of a disposable hospital gown.

Disposable diapers have been marketed which include an elastic or stretch member in the longitudinal side edges of the disposable diaper to provide elasticity about the leg of the infant when the diaper is applied. Examples of such stretchable fitted diapers which have elastic members disposed in the longitudinal side edges of the diaper are shown in U.S. Pat. Nos. 3,860,003 and 4,050,462. By being able to elastically contract the longitudinal sides of the diaper, which are the leg and thigh encircling portion of the diaper once placed on an infant, you can compress the diaper about the leg of the infant. By virtue of this compressing, you reduce leakage at the leg of the infant and the tighter you make the fit, the more you tend to reduce leakage. However, if the fit is too tight you will cause irritation on this tender portion of the thigh, especially when the diaper is wet. There are also a number of patents which disclose means for making the waist encircling portion of a disposable diaper elastic for tighter fit of the diaper about the waist of the wearer, for example, as shown and described in U.S. Pat. Nos. 3,995,637 and 3,995,640.

Disposable diapers usually comprise a facing and a backing layer which are substantially co-extensive and a somewhat smaller absorbent core or panel interposed between the facing and backing layer. The facing and backing layers are adhered together about their perimeter by hot melt adhesive or other adhesive material as is well known. In producing stretch or elastic diapers, an elastic member in its stretched or partially stretch state, is interposed between the facing and backing sheets along one or more edges of the diaper. The elastic member is adhered either to the facing and/or the backing sheets by adhesive or similar means and allowed to relax to produce elastic sections at the edges of the diaper. An example of a method for inserting elastic members in disposable diapers is disclosed in U.S. Pat. No. 4,081,301.

The incorporation of these elastic members into disposable diapers has increased both the cost of materials and construction of disposable diapers. With solid elastic members, it is necessary to adhere the side edges of the facing and backing sheets together, either directly or by their mutual attachment to the elastic member. Also, the use of the same adhesive throughout the process of incorporating the elastic members into the diaper to simplify its manufacture, require that the adhesive should be compatible with and have adhesive qualities with the elastic member, the plastic film backing material, and the soft textile facing material. In addition, when adhesively securing an unapertured elastic member into a disposable diaper, the adhesive chosen must be elastomeric or must be applied in a discontinuous pattern or the glue may make the diaper too stiff to gather. In contrast, the apertured elastic members of the present invention need not be adhered to either the facing or backing sheets, or are minimally adhered, and the adhesive used to secure the facing to the backing sheet need not be elastomeric and need be compatible with and have adhesive qualities with only the facing and backing sheets, and not the elastic member.

SUMMARY OF THE INVENTION

What we have discovered is an improved laminated structure adapted to be gathered for improved fit about a portion of a human body and a method of making the same. The laminated structure comprises first and second substrates of flexible, gatherable material and an apertured elastic member disposed between the substrates. The elastic member includes a plurality of interconnected elastic elements which define the apertures therebetween, and in the laminated structure the first and second substrates are secured together through at least some of the apertures. The laminated structure of the present invention may be used in any fitted garment but perhaps, is most suited for use in inexpensive and disposable apparel. The laminated structure can be incorporated into the sleeve cuff, the leg encircling portion, about the neck, and the waist of an article of apparel. In particular, the laminated structure may be incorporated into both the waist and thigh encircling portions of a disposable diaper or other disposable undergarments. The improved laminated structure of the present invention reduces the pressure applied to the skin of the wearer, and, in a disposable diaper or a disposable undergarment reduces the possibility of irritation and rash when wet. Surprisingly, the apertured elastic member can be readily inserted between the first and second substrates and these substrates easily adhered together to hold the elastic member in place, at high speeds, with good reliability and at reduced costs.

Furthermore, using the apertured member of the present invention in a laminated structure with adherence of layers through the apertures of the member allows for reduced thickness of the final laminated structure as compared to a similar structure using a solid elastic member wherein there must be an extra layer or thickness of adhesive on one or both surfaces of the solid member. This reduced thickness of the laminate along with the apertures in the elastic member provide for overall reduced forces in the final product mainly because of the reduced mass of the portion of the product to be gathered. This combination of reduced thickness and apertures also unexpectedly produces a more uniform distribution of the elastic forces which directly transmits into better conformity and improved fit about the extremity of the wearer; e.g., the leg of a wearer in a diaper product.

In accordance with the present invention, my improved laminated structure comprises first and second substrates of flexible, gatherable material and an apertured elastic member which includes a plurality of interconnected elastic elements defining the apertures therebetween. The first and second substrates are secured together through at least some of said apertures. Preferably, the elastic member has a width from about ¼ inch to about 1½ inches and the member may have a thickness of from 1 to 50 mils and preferably from about 5 to 20 mils. The elastic member may be made of any of the standard film materials which are stretchable and are recoverable and have a modulus of elasticity at 100 percent elongation of from about 20 to 2000 lbs./sq. inch. In a disposable diaper in accordance with the present invention, the elastic member may be disposed between the backing and facing sheet of the diaper in the longitudinal side edges of the diaper.

In one method of the manufacture of a disposable diaper incorporating the laminated structure of the present invention, the facing and backing sheets of the diaper are adhesively secured together as in the past; i.e., adhesive is placed on the backing and the absorbent core is secured to the central portion of the backing sheet and the facing sheet is adhered at the edges. The apertures of the elastic member, disposed in one or more of the edges of the backing, allow the adhesive disposed on the backing to adhere to the facing sheet through the apertures.

Also, when using our new apertured elastic member and adhering the facing to the backing through the apertures eliminates the need to adhere the facing to the backing outside the elastic member as is generally required when a solid member is used.

It should be pointed out that by using the reticulated or apertured elastic members in accordance with the present invention, the insertion of the member into the product and the adherence thereto is greatly simplified and, hence, has considerable economic benefit in the manufacturing process. The apertures or openings insure a uniform, intermittent lamination between the elastic and non-elastic layers and reduce the criticality of adhesive application. Also, the openings or apertures combined with adhesion of the layers through these openings or apertures provides that the final lamination acts or performs in its stretch, recovery and similar elastic properties substantially the same as the original reticulated or apertures member, thus allowing for greater certainty in predicting the quality and functionality of the final product. In contrast to this, when using a solid elastic member, its performance in the final product with regard to stretch, recovery and similar elastic properties altered by the manner and degree of adhesion of the non-elastic layers and by the properties of the non-elastic layers.

Furthermore, when an elastic member according to the present invention having longitudinally and transversely extending elements defining square or rectangular shaped apertures therebetween, is stretched in the longitudinal direction, there is no "necking down" of the member; i.e., reduction in the transverse dimension of the member. This transverse stability provides considerable advantages in the new and improved method for inserting elastic members in laminates according to the present invention as is very easy to align the elastic member in a stretched condition at or near the edge of the material to which the member is to be laminated. Also, on relaxation of the elastic member, there is no widening of the member and concomitant widening of the bonds securing the member to the material to which it is laminated.

DESCRIPTION OF THE PREFERRED EMBODIMENTS

For a laminated structure of the present invention, the apertured elastic member is a readily stretchable, preferably thermoplastic member that possesses a certain minimum elastic recovery.

The term "elastic", as used herein, refers to sheets, films, ribbons, filaments, and the like with apertures which have a recovery of at least 90 percent, when elongated to within 10 percent of their yield point and measured in accordance with the following formula:

$$\text{Percent Retraction} = \frac{L_e - L_t}{L_e - L_o} \times 100$$

where;

$L_o$=original length of sample
$L_e$=fully extended length $L_t$=length of sample measured three seconds after release from extended length The thickness of the elastic member may be from about 1 to 50 mils and is preferably from about 5 to about 20 mils. They have a width of from ¼ inch to 2 inches and preferably in diaper applications widths of from ½ inch to 1 inch have been found satisfactory. For ease of stretchability, the modulus of elasticity of the elastic member at 100 percent elongation should not exceed about 2000 lbs./sq. inch. The modulus of elasticity is preferably substantially less than 2000 lbs./sq. inch, and most preferably is about 75 to about 400 lbs./sq. inch.

Figures 1, 2:
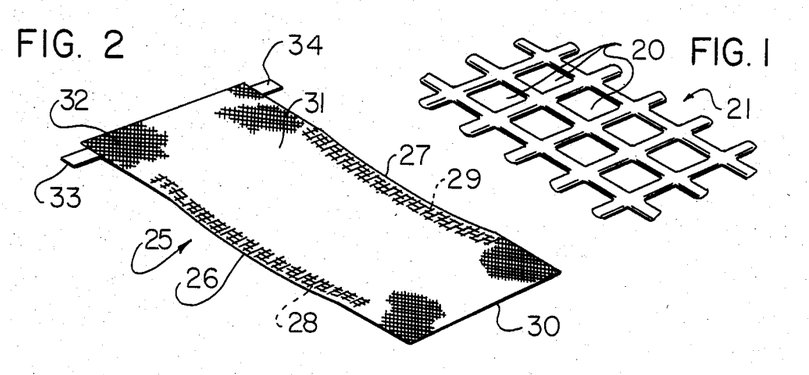
FIG. 1 is an enlarged perspective view illustrating a reticulated elastic member which may be used in one embodiment of the laminated structure of the present invention.
FIG. 2 is a perspective view illustrating a disposable diaper in accordance with the present invention, with the diaper laid out flat.

The term "reticulate", as used herein, refers to a construction having openings or apertures, substantially uniformly distributed therein to produce a net-like construction. As shown in FIG. 1, the openings or apertures 20 in the reticulated elastic member 21 may be rectangular in shape; however, the rectangular or square configuration is not essential to the present invention and the openings may have round, oval, or other various shapes. The "apertured" elastic members of the present invention need not have the symmetrical, regular array of rectangular-like apertures of a reticulated member, but may merely include a plurality of interconnected elastic elements defining apertures therebetween. Depending on the modulus of elasticity of the material used and the thickness and width of the member, the number of openings may vary from two to 100 openings per linear inch in both the longitudinal and transverse direction of the member. In addition, the elastic elements may be of different widths in the longitudinal or transverse direction, and the spacing between the elastic elements may vary from the transverse to the longitudinal direction.

Figures 3, 4:
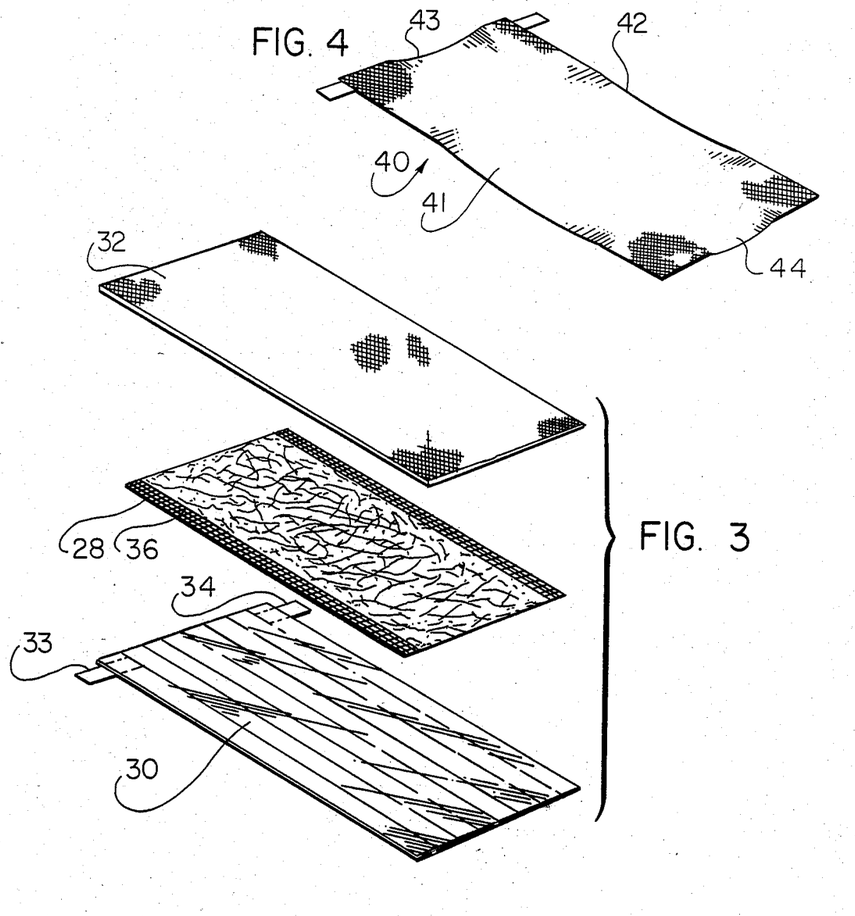
FIG. 3 is an exploded perspective view showing relative positioning of the diaper elements depicted in FIG. 2.
FIG. 4 is a perspective view of another embodiment of the disposable diaper embodying the present invention.

Referring to FIG. 2, a disposable diaper 25 embodying the present invention has longitudinal side margins 26 and 27. The central portion of each side margin is elastic to provide improved fit about the baby's thighs. The elastic member 28 and 29 in each of the longitudinal side margins is a reticulated film member according to the present invention. Individual components of the disposable diaper of FIG. 2 are illustrated in FIG. 3. The diaper additionally includes a first layer or backing layer 30 made of a moisture-impermeable material, a rectangular absorbent batt 31 superimposed over backing layer 30 and secured thereto by a series of glue lines deposited on the backing layer, and a second layer or facing layer 32 made of a moisture-permeable web and positioned in superimposed relationship to the absorbent batt. The absorbent batt is of smaller area than the backing and when substantially centered to the backing, is spaced from the longitudinal sides as well as the transverse ends of the diaper. The absorbent batt is flanked on its longitudinal sides by reticulated elastic members 28 and 29 located generally parallel the longitudinal side margins of the batt, and which, in an extended state, are secured between the backing and the facing by means of the adhesive lines. A moisture-pervious facing 32 is superimposed over the absorbent batt and secured to the backing by means of the end and side portions of the glue lines. The facing is also secured to the backing between the openings in the reticulated film member. For securing the diaper about a baby, the diaper is provided with pressure sensitive tape tab members 33 and 34.

In the manufacture of the diaper, only the central portions of the reticulated members 28 and 29 remain elastic and are secured between the facing and the backing. It should be noted the end portions of the elastic member which are not adhered to the facing and/or backing may be reticulated or not as desired. The use of a reticulated or apertured elastic member provides a reduction in cost of materials over a solid elastic member of the same length and width used to apply a gathering force to the longitudinal side margins. The reticulated elastic member of the present invention may be produced by a variety of methods such as by-passing an appropriate stretchable and recoverable film between the nip of a pattern forming roll and a back-up roll in a procedure analogous to that shown in U.S. Pat. Nos. 3,881,381 and 3,632,269.

Figure 14:
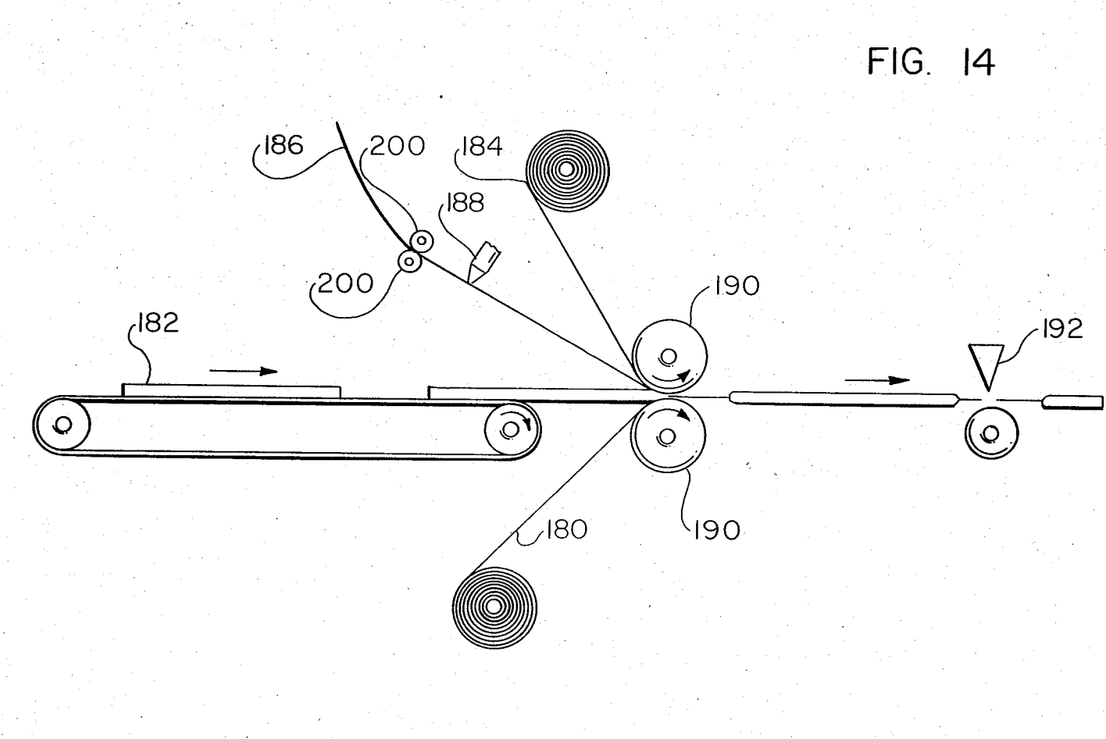
FIG. 14 is a schematic representation of one embodiment of a method of assembling the components of a disposable diaper according to the present invention.

A technique that may be used in the manufacture of the diaper in accordance with the present invention is to apply the adhesive directly to the reticulated elastic member along the portion desired to be adhered between the backing and facing members. Another technique is to apply adhesive to that portion of the backing or facing layer to which the elastic member is to be secured. In assembling the diaper, pressure is applied to the diaper in the region of the elastic member to adhere the facing and backing together between the openings in the elastic member. The components of a disposable diaper may be assembled according to one embodiment of the present invention as shown in FIG. 14. The backing layer 180, the absorbent pads 182, the facing layer 184, and the continuous ribbon of elastic members 186 are brought to an assembly station. The elastic members are stretched on their way to the assembly station by running nip rollers 200 at a speed lower than that of compressing roller 190. In this embodiment, adhesive is applied to the elastic members by nozzle 188. Pressure is applied to the diaper assembly in the region of the elastic members, by passing at least those regions through the nip of compressing rollers 190. In a particularly preferred embodiment, the surface of one of the rollers may be resilient.

The pressure applied to the diaper to adhere the backing layer to the facing layer may also squeeze adhesive through the openings in the elastic members, allowing one to adhere the backing to the facing when adhesive is originally applied to only one of the backing layer, the facing layer, or one surface of the elastic member.

It is desirable, to aid in insuring that the facing and backing are adhered together through the openings in the elastic member, that the upper or top compressing roller 190 be made of a very resilient material or have a very resilient covering as its outer surface. The resilient surface allows the roller surface to deflect into the openings of the elastic member and press together the thin areas where only facing and backing layers are present.

The portion of the elastic member not secured by the diaper components may be allowed to retract inside the diaper between the facing and backing and remain there.

There are a number of ways that retraction of a portion of the elastic member without gathering the layers of material may be accomplished. One such technique is to secure the elastic member with the facing and/or backing layers only over a portion of the member. When the member is subsequently severed in an unsecured portion, such as by a cutting knife 192 and back-up roller anvil to produce individual diapers, the unsecured portion of the member will retract to an area where the member is secured with the facing and/or backing layers. Such retraction will have no gathering effect on the facing and backing layers. The elastic member may be left unsecured to the facing and backing layers at certain portions by a number of techniques such as not applying adhesive to specific areas or eliminating the compression in specific areas until after the member has been severed or treating a portion of the elastic member with a release agent such as a silincone so that it will not adhere to the facing and backing layers or other similar processes for rendering a portion of the elastic member ineffective to gather the facing and backing layers.

As previously mentioned, an important and unexpected advantage of using our new reticulated elastic member, having square or rectangular shaped openings, is that the member does not "neck down"; i.e., reduce its width or transverse dimension when stretched in the longitudinal direction. As can be appreciated, this is extremely important since the elastic member is in a longitudinally stretched condition when assembled in the diaper. The elimination of the necking down phenomena allows the member to be positioned with accuracy. The elastic member may be placed at the extreme outer edge of the facing and backing layers to allow for complete use of the layers in the final product without having to trim the edges and without excess material extending beyond the elastic member. Furthermore, the tolerance required to obtain suitable insertion of the elastic member into the diaper are reduced. The above advantages simplify the method of manufacture of the diaper and provide improved yields in manufacture both of which are economically beneficial.

FIG. 4 shows another disposable diaper 40 similar to that shown in FIG. 2 with the exception that all four edge portions; that is, the two longitudinal side margins 41 and 42 and the front 43 and rear 44 end portions all have reticulated elastic members inserted between the facing and the backing with the central portions thereof elastic.

Figures 5, 6, 7, 8:
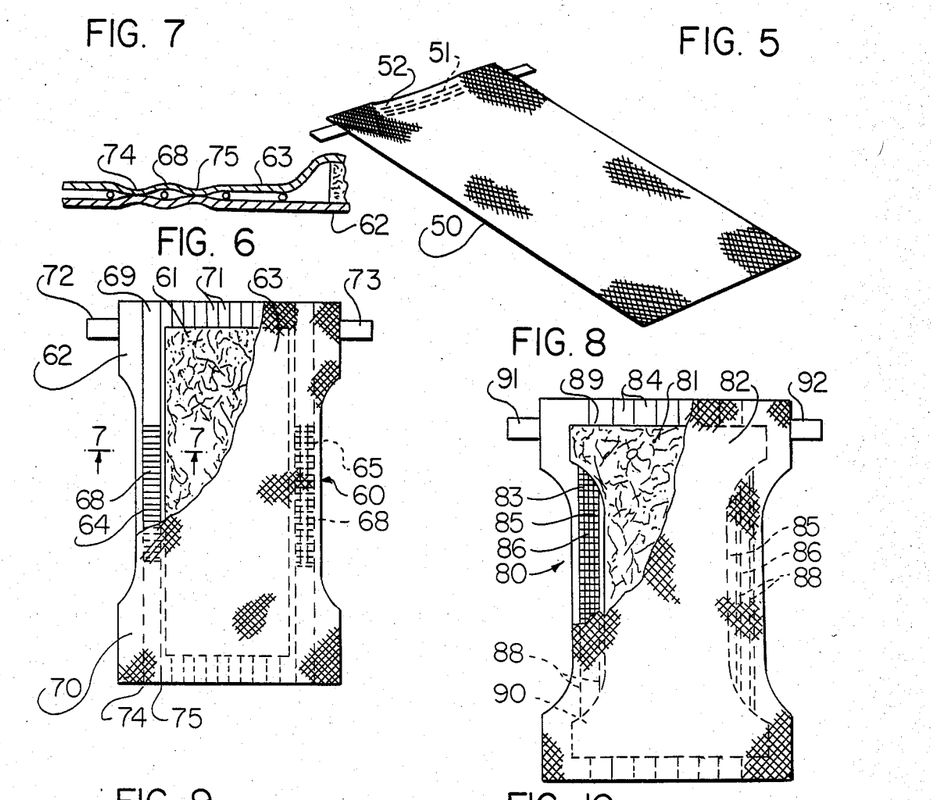
FIG. 5 is a perspective view showing still another embodiment of the disposable diaper embodying the present invention.
FIG. 6 is a plan view of one embodiment of the disposable diaper of this invention with a portion broken away to show interior detail.
FIG. 7 is an enlarged cross-sectional view taken along line 7—7 of FIG. 6.
FIG. 8 is a plan view of another embodiment of the disposable diaper of this invention with a portion broken away to show interior detail.

FIG. 5 shows a disposable diaper 50 similar to the diaper depicted in FIG. 2 with the exception that the reticulated elastic member 51 is in the central front waist portion 52 of the diaper to provide improved fit about the baby's waist.

In the embodiment shown in FIG. 6, a disposable diaper 60 is provided with a substantially rectangular panel 61 sandwiched between a backing 62 and facing 63 and together with the backing and facing define side margins 64 and 65. Curvilinear cut-outs are provided in the respective central side portions of the facing and backing for further fit enhancement. Pre-stretched reticulated thermoplastic elastic members 68 are positioned in the longitudinal side margins and are secured to the backing and facing along the longitudinal sides of the absorbent panel. The reticulated elastic members have been rendered inelastic at their end positions 69 and 70. A technique for rendering the end of a thermoplastic elastic member inelastic is to heat the end sufficiently to remove the elastic property of the thermoplastic material in the heated area. Such a technique along with the related techniques which may be used to render portions of elastic members inelastic are disclosed and described in the co-pending commonly assigned patent application Ser. No. 106,336 filed Dec. 21, 1979, which is incorporated herein by reference. Glue lines 71 secure the facing and absorbent panel to the backing and adhesive tape tabs 72 and 73 provide diaper securement means.

Referring to FIG. 7, which is a cross-sectional view taken along line 7—7 of FIG. 6, there is shown the impervious backing member 62 with the reticulated elastic ribbon 68 secured between the backing member and the facing member 63 by the glue lines 74 and 75.

In the embodiment shown in FIG. 8, the disposable diaper 80 is provided with an absorbent batt 81 and also having curvilinear side cut-outs and sandwiched between facing 82 and backing 83 having similar cut-outs. Glue lines 84 serve to secure the batt and facing to the backing. Reticulated elastic ribbons 85 are situated in the general rectilinear diaper side margins. The reticulated elastic ribbons are secured between the facing and backing at the central portion 86 by adhesive lines 88 which may be applied at the same time as, and may lie along the same line as certain of the glue lines 84.

Protruding portions 89 and 90' of the absorbent batt overlap into the four corners of the diaper and prevent the elastic member from being secured to the facing in those areas. The prevention of the adherence of the end portions of the elastic member may be accomplished in a number of other ways.

Another technique is to apply the adhesive in a suitable pattern so that it does not contact the reticulated elastic members at the end portions thereof.

Figure 9:
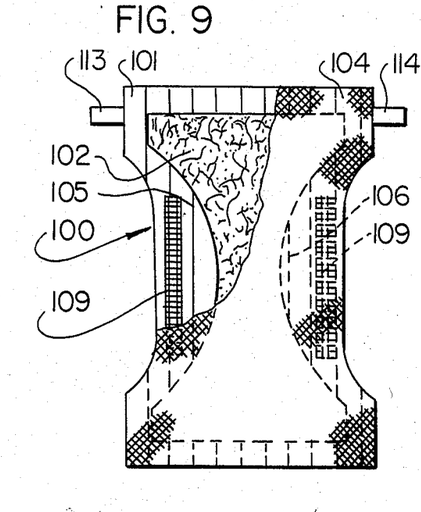
FIG. 9 is a plan view of still a further embodiment of a disposable diaper of this invention with a portion broken away to show interior detail.

Yet another technique is to burn out or remove the elasticity from the end portions by the application of heat or other energy to those portions, such as the method desribed in co-pending Application Ser. No. 106,336 hereinbefore incorporated by reference. The tape tabs 91 and 92 are secured to the backing to provide means for securing the diaper to the baby. In the embodiment shown in FIG. 9, the disposable diaper 100 of the present invention comprises an impervious backing member 101, an hour-glass shaped absorbent pad 102, and a top facing layer 104. In this configuration, the top layer and impervious backing layers form areas 105 and 106 as part of the side margins. These areas of the side margins contain no absorbent core material. This reduces the bulk of material between the baby's legs. In each side of the diaper, there is inserted between the impervious backing layer and pervious facing layer a reticulated elastic member 109. The diaper has an hour-glass shaped absorbent body wherein the absorbent body in the waist portion is wider than the absorbent body in the crotch area. At the back waist portion of the diaper, there are adhesive tape tabs 113 and 114 adhered to the backing member.

Figure 10:
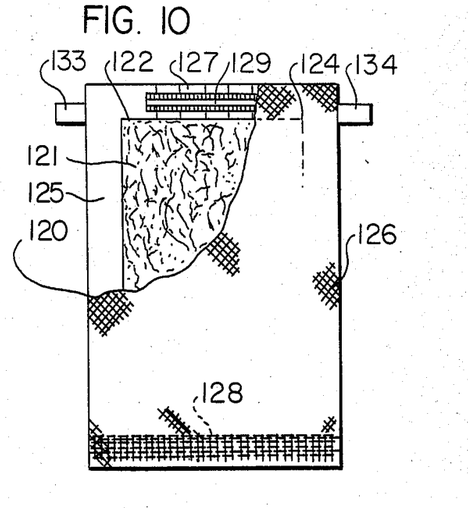
FIG. 10 is a plan view of an additional embodiment of a disposable diaper of this invention with a portion broken away to show interior detail.

The embodiment shown in FIG. 10 is a disposable diaper 120 which comprises a rectangular impervious backing member 122 with a smaller area of absorbent core 121 adhered thereto with glue lines applied to the backing member. On top of the absorbent core is the facing member 124 which is co-extensive with the backing member to form the longitudinal side margins 125 and 126 and the end margins 127 and 128.

In a preferred construction, reticulated elastic member 129 is adhered between the backing and facing members at the back waist margin 127. A similar reticulated elastic member may also, if desired, be inserted in the front waist margin 128 of the diaper. The adhesive tape tabs 133 and 134 are adhered to the backing member and are used for securement of the diaper about the baby.

The elastic members suitable for use in the diapers contemplated may be made from films extruded, calendered, or otherwise formed to the desired thickness and pattern of openings utilizing low stretch modulus materials made from any rubbery elastic material. Specifically unvulcanized thermoplastic compositions which are made of an elastomeric component and an optional compatible modifier which is a thermoplastic polymer of a relatively low molecular weight but solid at ambient temperatures have been found to make suitable elastic members for use in accordance with the present invention.

Illustrative of the elastomeric components suitable for present purposes are block copolymers which comprise terminal thermoplastic polymer blocks and at least some non-terminal or intermediate elastomeric polymer blocks. Block copolymers of this general type may be prepared using a step-wise polymerization initiator, e.g., an organolithium compound. Such block polymerization techniques are well known in the art.

The elastic component can be linear or radial $A^1$—B—$A^2$ block copolymers or mixtures thereof with simple $A^1$—B block copolymers wherein $A^1$ and $A^2$ can be alike or different and represent a thermoplastic polymer block, such as poly (vinyl arene) block, and B represents an elastomeric polymer block such as a conjugated diene or a lower (i.e., $C_1$—$C_4$) alkene. The modifier component is a low molecular weight thermoplastic polymer having an average molecular weight of about 500 to 7,500 and is present in the composition in an amount of about zero to about 200 parts by weight per 100 parts by weight of the elastomeric component.

A preferred thermoplastic film composition for the elastic members comprises an elastomeric component which contains, as a major constituent thereof, an unvulcanized linear block copolymer of the general configuration, $$A^1-B-A^2$$

wherein $A^1$, $A^2$ and B have the same meaning as hereinabove. In these block copolymers, the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to 200 parts by weight per 100 parts by weight of the elastomeric component.

The preferred $A^1$—B—$A^2$ block copolymers have A-blocks derived, i.e. polymerized or copolymerized, from styrene or styrene homologues; and B-blocks derived from conjugated dienes, such as isoprene or butadiene, or from lower alkenes such as ethylene and butylene. Small proportions of other monomers also may enter into the block copolymers themselves. The individual A-blocks can have an average moleular weight of at least about 6000, preferably in the range of about 8000–30,000, and the A-blocks constitute about 5–50 percent, preferably about 10–30 percent, by weight of the block copolymer. The average molecular weight of the B-blocks for linear $A^1$—B—$A^2$ block copolymers preferably is in the range of about 45,000–180,000 and that of the linear copolymer, itself, preferably is in the range of about 75,000–200,000. The average molecular weight of the radial $A^1$—B—$A^2$ block copolymers preferably is in the range of about 125,000–400,000. The term "linear block copolymer" (or copolymers) includes branched $A^1$—B—$A^2$ copolymers as well as unbranched $A^1$—B—$A^2$ copolymers.

The radial $A^1$—B—$A^2$ copolymers useful for manufacture of elastic members for diapers of this invention are of the type described in U.S. Letters Pat. No. 3,281,383 to Zelinski, et al. and conform to the following general formula: $(A-B-_nX)$, wherein A is a thermoplastic block polymerized from styrene or styrene homologues, B is an elastomeric block derived from conjugated dienes or lower alkenes, as indicated above, X is an organic or inorganic connecting molecule with a functionality of about two to four as described in U.S. Pat. No. 3,281,383, or possibly with a higher functionality as described in the Article entitled "New Rubber is Backed by Stars" appearing on Page 35 of the June 11, 1975, issue of Chemical Week. As used hereinabove, "n" has a value corresponding to the functionality of X.

The preferred elastic member is highly thermoplastic and, though elastomeric, is unlike rubber in that it exhibits a relatively sharp melting point and is capable of being heat shaped. Also, the elastic member can form permanent heat seals to substrates such as non-woven fabrics or the like, at relatively low heat sealing temperatures, generally not above about 350° F. The member is very flexible, extensive and soft, and normally exhibits a Gurley stiffness of about one or less at a film thickness of one mil.

Elastic members especially suitable for use in disposable diapers may be made from combinations of thermoplastic rubber and amorphous polypropylene. The thermoplastic rubbers used in such combinations are block copolymers having blocks of polybutadiene or polyisoprene, and blocks of polystyrene. A review article discussing these materials is "Structure and Properties Of Block Polymers And Multiphase Polymer Systems: An Overview of Present Status And Future Potential", by S. L. Aggarwal, *Polymer,* Vol. 17, Nov. 1976, Pages 938–956. Two representative types of themoplastic rubbers useful in these combinations are the linear block copolymers (A—B—A) having a mid-block of polybutadiene or polyisoprene and end-blocks of polystyrene, and the "star" or "radial" block copolymers having from 4 to 20 "arms" connected to a common center. Each arm is an A—B block copolymer, the inner portion being polybutadiene or polyisoprene, with the outer portion being polystyrene.

The material added or combined with the thermoplastic rubber, primarily to improve processability, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. The exact minimum amount of amorphous polypropylene which must be employed varies somewhat from case to case, but it is usually of the order of about 10 weight percent, based on weight or rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis), a significant reduction in the characteristic rubbery elastomeric properties of the product begins to occur. This may be acceptable for some uses, and not for others. Thus, the upper limit of amorphous polypropylene would be that point at which the product still retains significant rubbery elastomeric characteristics.

Other conventional materials, employed in the usual amounts, can be employed in the mixture for their known purposes. Such materials include pigments, anti-blocking agents, stabilizers, anti-oxidants, ultraviolet stabilizers, bonding aid, and the like.

Especially suitable reticulated elastic material which may be used in accordance with the present invention are those described in U.S. Pat. No. 4,329,309 to William G. F. Kelly. A specific reticulated elastic member which we have found suitable for producing the disposable diapers of the present invention is that described in Example 2 of the aforementioned patent wherein the reticulated elastic member has the following composition:

|  | Parts by Weight |
| --- | --- |
| Solprene 418 | 66.9 |
| Solprene 414 | 20.0 |
| Elvax 460 or UE 630 | 8.0 |
| Kenamide E | 0.8 |
| Ionol (anti-oxidant) | 0.2 |
| Irganox 1010 (anti-oxidant) | 0.2 |

"Solprene P414" is a 60/40 butadiene/styrene radial block copolymer, and "Solprene P418" is an 85/15 isoprene/styrene radial block copolymer. These materials are further characterized as follows:

|  | Solprene P414 | Solprene P418 |
| --- | --- | --- |
| Molecular weight | 150,000 | 300,000 |
| Specific gravity | 0.95 | 0.92 |
| Melt flow, 5 kg @200° C. | 2.2 | 2.2 |
| Inherent viscosity | 0.80 | 1.16 |
| Solution viscosity, cps. |  |  |
| 20% wt in toluene | 230 | 900 |
| 25% wt in toluene | — | 2300 |

"Elvax" 460 is an ethylene/vinyl acetate copolymer having a Melt Index (by ASTM D 1238) of 2.2–2.8 and a vinyl acetate content of 17.5 to 18.5 weight percent. "Petrothene" UE 630 is an ethylene/vinyl acetate copolymer having 17 weight percent vinyl acetate and a Melt Index of 0.5.

"Kenamide E" is a fatty acid amide.

In some embodiments of the disposable diaper of the present invention, the elastic member is a member which may be made elastic by imparting heat or other forms of energy to the member to shrink the member and provide it with elastic characteristics. A portion of the member is so treated to provide the elastic means while other portions are not treated.

The heat-shrinkable films which may be used as elastic members in the disposable diapers of the present invention may be the polyolefin films which have been oriented to a degree and which will then become elastic when heat shrunk. Usually, a preferred technique for orienting the polyethylene film to provide the heat shrunk elastic properties is by irradiation such as suggested in British Patent No. 866,820. Also useful as the heat shrunk elastic members are the copolymers of ethylene and vinyl acetate, ethylene and ethyl acrylate, and the like. The forming of such copolymers is well known and specific methods of forming such materials are disclosed in U.S. Pat. Nos. 2,200,429 and 2,953,551. After the copolymer is formed and made into a film, it is given the proper orientation as described in the previously mentioned British Patent No. 866,820.

The apertured elastic member useful in accordance with the present invention may also be made from other materials; such as, natural rubber, the synthetic rubbers, and the like. The member may be made in the form of a film with intermittent longitudinal portions that are reticulated separated by non-reticulated portions. The film is slit into the desired width and inserted between the backing and facing sheet of the diaper.

Broadly, the elastic members may be made from materials having elongations of from 20 to 1000 percent and preferably from about 50 to 500 percent with recoveries in the range of 20 to 100 percent and preferably from 70 to 100 percent. The material should have a force to stretch it 100 percent of from 30 to 2000 grams.

The important factor to remember is that when the material is placed in the end product, the material be elastic, as previously defined, so it functions as such an elastic in the final product. For example, in the diaper leg band area, the member should have 90 percent or better recovery in very short periods of time and preferably almost simultaneously, the member should also require a relatively low amount of force to stretch the leg band area back to its original or non-gathered length. Such force should be less than 200 grams and may be as low as 20 grams.

The apertured elastic member may be adhered in the diaper by placing the adhesive on the backing and placing the apertured member on the adhesive. The facing layer is placed on top of the apertured member and pressure is applied by means of a roll to cause the adhesive to pass through the openings in the member and adhere at least the facing and backing together. Another technique is to place the adhesive on either or both sides of the elastic member and place the backing and facing on opposite sides and press together to cause the backing and facing to adhere.

When the facing and backing are adhered together through the apertures in the elastic member, it is not necessary to adhere the facing and backing together outside the elastic member. In fact, when the facing and backing are not adhered together outside the elastic member, the edge of the diaper takes on a soft and pleasing ruffled effect along its edge.

Though only the rectangular elastic members have been discussed above, it should be appreciated the elastic members could be shaped or curved as desired depending on the desired shape of the final garment.

Figure 11:
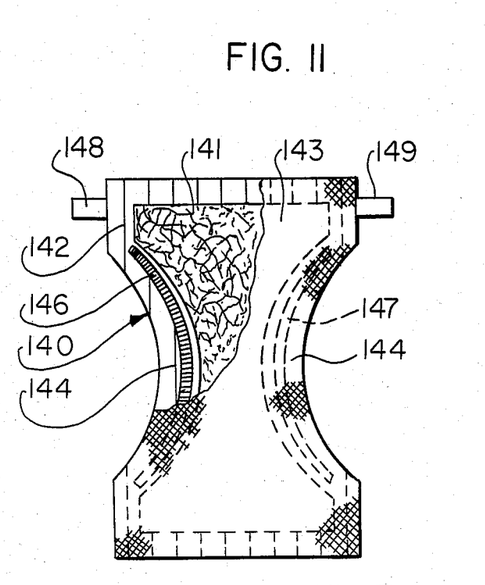
FIG. 11 is a plan view of yet another embodiment of this invention with a portion broken away to show interior detail.

The disposable diaper 140 illustrated in FIG. 11 has an hour-glass shaped absorbent batt 141, a moisture-impervious backing layer 142, and a moisture-permeable facing layer 143. The diaper 140 has side marginal portions 144 with curvilinear reticulated elastic members 146 and 147 disposed therein. The facing and backing layers are cut out as shown to give the diaper an hour-glass configuration. The facing and backing layers may be adhered to each other through the apertures of the elastic members and/or may be attached to the elastic member. Tape tabs 148 and 149 are provided for securing the diaper about the waist of the wearer.

Figure 12:
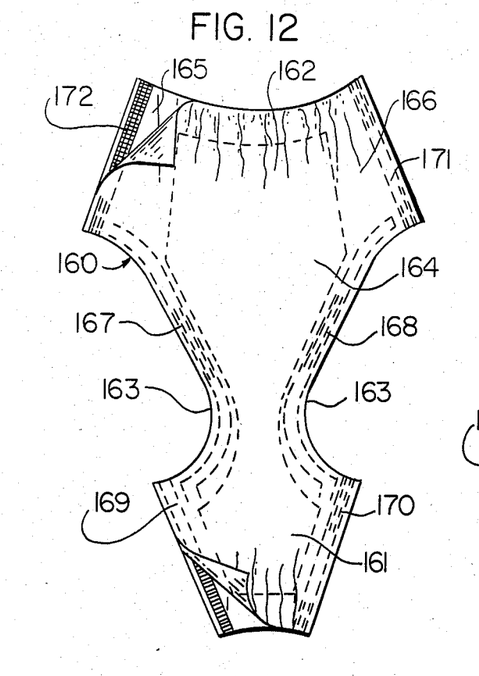
FIG. 12 is a plan view of a disposable undergarment laid out flat, in accordance with the present invention with portions folded back to show interior detail.

FIG. 12 illustrates a disposable undergarment 160 suitable for use in toilet training infants, or by incontinent children or adults. The undergarment has a front portion 161, a rear portion 162, and a crotch portion 163 comprised of an intermediate liquid absorbent panel 164 disposed between outer layer 165 and a moisture-permeable inner layer 166. The waistband of the undergarment may be gathered by a reticulated elastic member(s) located between the ends of the inner and outer layers at the rear portion and optionally between the ends of the inner and outer layers at the front portion. The undergarment may also be provided with reticulated elastic members 167 and 168 disposed between the inner and outer layers at the side margins of the crotch region.

Figure 13:
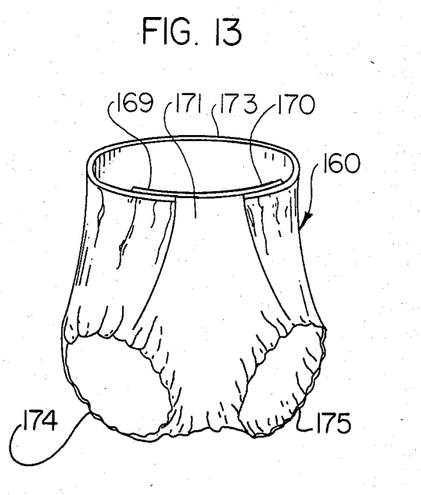
FIG. 13 is a perspective view of the disposable undergarment of FIG. 12 viewed in the configuration it assumes when disposed about a wearer.

FIG. 13 illustrates the disposable undergarment 160 of FIG. 12 about a wearer in use; both side margins 169 and 170 of the front portion being joined to respective side margins 171 and 172 of the rear portion to define a waist portion 173 and self-fitting leg apertures 174 and 175.

Several different types of facing materials may be used for the disposable undergarment, for example, the facing may be a non-woven web made of a mixture of fibers consisting predominantly of inexpensive, short, cellulosic fibers such as short wood pulp fibers or cotton linters in amounts of 75 percent to 98 percent, the balance being textile length fibers such as rayon as described in U.S. Pat. No. 3,663,348 to Liloia, et al.

Non-woven facing materials suitable for us in disposable undergarments of this invention can have fabric weights in the range of from about 0.5 to 5 ounces per square yard and densities of less than 0.15 g./cc., generally in the range of 0.05 to about 0.1 g./cc. The dry strength of the facing sheet for a fabric having a weight of about 1.5 ounces per square yard is at least 0.15 lbs. per inch of width in the machine direction and at least 0.1 lb. per inch of width in the cross direction. Such fabrics have good elongation, loft, softness, and drape characteristics. Facings may also be made of an apertured non-woven fabric which is formed, for example, in accordance with the teachings of commonly assigned U.S. Pat. Nos. 2,862,251; 3,081,514; and 3,081,515. Furthermore, facings may also be made from other types of fabric such as those disclosed and described in U.S. Pat. No. 3,485,706 to Evans. Such facings can be made of naturally occurring fibers, synthetic fibers or blends thereof. Typical facing sheets made of polyester type fibers may have a weight of about 0.75 ounces per square yard.

The facing may be the same size as, and coterminous with, the backing; or alternatively, the facing may be wider than the backing and have its side edges inwardly folded so that the facing is coterminous with the backing, as is shown in FIG. 3 of U.S. Pat. No. 3,612,055. In the latter case, the elastic members may be secured above the inwardly folded side edges of the facing. In addition, facings may be made from non-apertured materials such as non-woven isotropic webs or apertured polyolefin or polyester films having the desired moisture permeability. In all of the aforementioned facings, the materials should be relatively hydrophobic so as to retard wicking within the facing.

The moisture absorbent batt or panel of a desired shape, but smaller than the facing and backing, can be formed in accordance with the teachings of U.S. Pat. No. 3,612,055 to Mesek, et al.

A suitable backing material for the disposable undergarments embodying the present invention can be an opaque polyolefin; for example, polyethylene about 0.001 inch thick. Another suitable material for this purpose is polyethylene terephthalate having a thickness of about 0.005 inch.

In use, the disposable diaper is applied to the baby by laying out the diaper on a single flat surface and placing the baby thereon. The waist underlying end of the diaper is that end having the fastener means and the other end of the diaper extends downwardly between the baby's legs.

Next, the downwardly extending end of the diaper is brought up between the baby's legs to a position covering the perineum and contiguous with the front portion of the baby's waist. The diaper thereafter is secured to the baby by placing the corners of the waist portion of the abdomen covering end as far around the baby's waist as they will go and by bringing the corners of the underlying end of the diaper into an overlapping relationship with the aforementioned corners so that the diaper snugly encircles the baby's waist and provides a custom fit. The adhesive tape fasteners are then prepared for use and the diaper is brought in a desired position by simply urging the pressure-sensitive adhesive surface of the tape tab in contact with the adjacent outer surfaces of the opposite corner of the diaper.

In some instances, it may be desirable to have a second fastener available that can be applied just above the thigh of the infant and below the standard fastener to improve and secure the fit of the stretch diaper.

The foregoing description of the drawings are illustrative and are not to be taken as limiting. Still other variations and modifications are possible without departing from the spirit and scope of the present invention.

What is claimed is:

1. A laminated structure adapted to be gather for improved fit about a portion of the human body comprising: first and second layers positioned adjacent to one another, said layers being formed of flexible gatherable material, an elastic member disposed between said layers, said elastic member consisting of longitudinal and transverse interconnected elastic elements and being reticulated with apertures comprising a net-like construction, said second and first layers being secured together through at least some of said apertures.

2. A laminated structure as in claim 1 wherein the first and second layers comprise a single piece of folded material.

3. A disposable diaper comprising: a moisture-permeable facing layer; an absorbent panel at one side of said facing layer, said absorbent panel being smaller than said facing layer so that marginal portions of the facing layer extend outwardly beyond the edges of said absorbent panel; a moisture-impervious backing layer at the side of said absorbent panel opposite said facing layer, said backing layer being larger than said absorbent panel so that marginal portions of the backing layer extend outwardly beyond the edges of said absorbent panel; means bonding said facing and backing layers to one another; and gathering means disposed in at least one marginal portion, said gathering means being an apertured elastic member consisting of longitudinal and transverse interconnected elastic elements in reticulated form, secured by bonding said facing and said backing together through at least some of said apertures.

4. A disposable diaper as in claim 3 wherein the means bonding the facing and backing layers together does not extend outboard of the gathering means.

5. A unitary, multi-layer, disposable undergarment, suitable for use in training infants or by incontinent children or adults, which is constructed from a nonwoven fabric and comprises a front portion, a rear portion and a crotch portion connecting said front and rear portions; both side margins of said front portion being joined to respective side margins of said rear portion so as to define a waist portion and leg apertures, said undergarment having a moisture-pervious inner layer adapted to contact the wearer's skin, an outer layer and an intermediate liquid absorbent panel disposed therebetween, and an elastic member disposed between the ends of the inner layer and the outer layer at the rear portion, said elastic member consisting of longitudinal and transverse interconnected elastic elements and being reticulated with apertures comprising a net-like construction, said inner layer and said outer layer being secured together through at least some of said apertures.

6. A disposable undergarment as in claim 5 having an elastic member disposed between the ends of said inner layer and said outer layer at the front portion, said elastic member consisting of longitudinal and transverse interconnected elastic elements and being reticulated with apertures comprising a net-like construction.

7. A disposable undergarment as in claim 5 wherein said undergarment is also provided with elastic members disposed in the side margins of said crotch portion, each of said elastic members consisting of longitudinal and transverse interconnected elastic elements and being reticulated with apertures comprising a net-like construction, said inner layer and said outer layer being secured together through at least some of said apertures.

* * * * *

UNITED STATES PATENT AND TRADEMARK OFFICE
CERTIFICATE OF CORRECTION

PATENT NO. : 4,573,991
DATED : March 4, 1986
INVENTOR(S) : Heinz A. Pieniak and Virginia R. Mesek It is certified that error appears in the above-identified patent and that said Letters Patent is hereby corrected as shown below:

Col. 14, line 34: "gather" should read --gathered--.

Signed and Sealed this

Twenty-ninth Day of July 1986

[SEAL]

Attest:

Attesting Officer

DONALD J. QUIGG

Commissioner of Patents and Trademarks